United States Patent
Chen et al.

(10) Patent No.: US 9,633,432 B2
(45) Date of Patent: Apr. 25, 2017

(54) IMAGE ANALYSIS METHOD AND APPARATUS FOR ASSESSMENT OF PERITONEAL DIALYSIS COMPLICATION IN PERITONEAL DIALYSIS

(71) Applicants: National Tsing Hua University, Hsinchu (TW); National Taiwan University, Taipei (TW); National Taiwan University Hospital, Taipei (TW)

(72) Inventors: Hung-Shao Chen, Taichung (TW); Jenq-Wen Huang, Taipei (TW); Hsi-Pin Ma, Hsinchu (TW)

(73) Assignees: National Tsing Hua University, Hsinchu (TW); National Taiwan University, Taipei (TW); National Taiwan University Hospital, Taipei (TW)

(*) Notice: Subject to any disclaimer, the term of this patent is extended or adjusted under 35 U.S.C. 154(b) by 7 days.

(21) Appl. No.: 14/957,601

(22) Filed: Dec. 3, 2015

(65) Prior Publication Data
US 2017/0039700 A1     Feb. 9, 2017

(30) Foreign Application Priority Data
Aug. 5, 2015 (TW) .............................. 104125440 A

(51) Int. Cl.
*G06T 7/00* (2006.01)
*A61M 1/28* (2006.01)
(Continued)

(52) U.S. Cl.
CPC ............. *G06T 7/0012* (2013.01); *A61M 1/28* (2013.01); *G06T 5/20* (2013.01); *G06T 7/13* (2017.01);
(Continued)

(58) Field of Classification Search
CPC ... G06T 5/20; G06T 7/0012; G06T 7/13; G06T 7/09; G06T 2207/10024;
(Continued)

(56) References Cited

U.S. PATENT DOCUMENTS 7,955,295 B2 * 6/2011 Lee .......................... A61M 1/28
604/29
8,361,009 B2 * 1/2013 Lee .......................... A61M 1/28
604/29
(Continued)

FOREIGN PATENT DOCUMENTS

CN    102099065    6/2011
CN    103079076    5/2013
(Continued)

*Primary Examiner* — Katrina Fujita
(74) *Attorney, Agent, or Firm* — Jianq Chyun IP Office

(57) ABSTRACT

An image analysis method and an apparatus thereof for assessment of PD (peritoneal dialysis) complications in peritoneal dialysis are provided. An analysis procedure is executed on an image under test of a dialysis bag, so as to obtain a color location in a color space corresponding to the image under test. A prompt signal is sent when the color locations obtained in a time period gradually become close to a disease warning range after executing the analysis procedure on a plurality of images under test.

10 Claims, 3 Drawing Sheets

(51) Int. Cl.
*G06T 5/20* (2006.01)
*H04L 29/08* (2006.01)
*G06T 7/90* (2017.01)
*G06T 7/13* (2017.01)

(52) U.S. Cl.
CPC .............. *G06T 7/90* (2017.01); *H04L 67/1097* (2013.01); *A61M 2205/52* (2013.01); *G06T 2207/10024* (2013.01); *G06T 2207/30084* (2013.01)

(58) Field of Classification Search
CPC ...... G06T 2207/30084; H04L 67/1097; A61M 1/28; A61M 2205/52
See application file for complete search history.

(56) References Cited

U.S. PATENT DOCUMENTS

| | | | |
|---|---|---|---|
| 8,496,609 B2* | 7/2013 | Childers | A61M 1/14 417/477.2 |
| 8,512,275 B2* | 8/2013 | Childers | A61M 1/14 604/29 |
| 8,945,042 B2* | 2/2015 | Lee | A61M 1/28 417/477.2 |
| 9,242,034 B2* | 1/2016 | Childers | A61M 1/14 |
| 2010/0005416 A1* | 1/2010 | Hedmann | A61M 1/28 715/810 |
| 2013/0079706 A1 | 3/2013 | Childers et al. | |
| 2013/0131574 A1* | 5/2013 | Cosentino | A61M 1/16 604/6.07 |
| 2013/0303865 A1* | 11/2013 | Rebec | A61B 5/0082 600/310 |
| 2014/0129250 A1 | 5/2014 | Daniel et al. | |
| 2014/0233826 A1 | 8/2014 | Agaian et al. | |

FOREIGN PATENT DOCUMENTS

| | | |
|---|---|---|
| CN | 103079077 | 5/2013 |
| TW | 201328738 | 7/2013 |
| TW | I421795 | 1/2014 |

* cited by examiner

IMAGE ANALYSIS METHOD AND APPARATUS FOR ASSESSMENT OF PERITONEAL DIALYSIS COMPLICATION IN PERITONEAL DIALYSIS

CROSS-REFERENCE TO RELATED APPLICATION

This application claims the priority benefit of Taiwan application serial no. 104125440, filed on Aug. 5, 2015. The entirety of the above-mentioned patent application is hereby incorporated by reference herein and made a part of this specification.

BACKGROUND OF THE INVENTION

Field of the Invention

The invention relates to an image analysis technique and more particularly relates to an image analysis method and an image analysis apparatus for assessment of peritoneal dialysis complications in peritoneal dialysis.

Description of Related Art

Patients with chronic renal failure need long-term dialysis treatment. For these patients, peritoneal dialysis may be carried out at home and thus has the features of low cost and high efficiency, compared to hemodialysis which requires the patients to go to the hospital regularly. Therefore, peritoneal dialysis is being promoted. Peritoneal dialysis is to inject a dialysis solution into the peritoneal cavity and use the peritoneum to filter and remove waste generated by metabolism and excess water in the blood, which is a renal failure therapy in addition to hemodialysis.

The peritoneal dialysis recovered solution may present a different look depending on the physical condition of the patient. In other words, the doctor may check the peritoneal dialysis recovered solution to determine whether the patient using peritoneal dialysis has other complications. However, naked-eye visual inspection may not be efficient and effective for determining occurrence of complications. Moreover, complications such as peritonitis also raise concerns about use of peritoneal dialysis.

SUMMARY OF THE INVENTION

The invention provides an image analysis method and an image analysis apparatus for assessment of peritoneal dialysis complications in peritoneal dialysis for detecting a special complication before its occurrence.

The image analysis method of the invention includes the following: capturing an image under test of a dialysis bag; executing an analysis procedure on the image under test, wherein the analysis procedure includes: executing an edge detection on the image under test to obtain a region of interest, executing a color detection on a plurality of pixels included in the region of interest to obtain original color information corresponding to the region of interest, executing a color correction on the original color information to obtain corrected color information, converting the corrected color information to a color location in a color space, and comparing the color location with a plurality of disease warning ranges recorded in a database; continuing to capture another image under test of another dialysis bag drained from peritoneum next time and executing the analysis procedure on the another image under test; and sending a prompt signal when detecting that the color locations of a plurality of the images under test captured in a time period gradually becomes close to one of the disease warning ranges after continuously executing the analysis procedure on a plurality of the images under test.

In an embodiment of the invention, the image analysis method further includes: executing a linear regression calculation on red color, green color, and blue color of a plurality of color patches in a bottom row of a color checker to obtain a set of regressed color parameters; and executing the linear regression calculation on red color, green color, and blue color of all color patches of the color checker according to the regressed color parameters to obtain a color correction matrix. Further, the color correction is executed on the original color information based on the color correction matrix to obtain the corrected color information.

In an embodiment of the invention, the image analysis method further includes: uploading the image under test, the corrected color information, and a comparison result obtained by comparing the color location with the disease warning ranges recorded in the database to a cloud server.

In an embodiment of the invention, the color space is a CIE Lab color space.

In an embodiment of the invention, the step of executing the color detection on the pixels included in the region of interest to obtain the original color information corresponding to the region of interest includes: respectively extracting red color, green color, and blue color from each of the pixels of the region of interest to obtain three color arrays; and retrieving an average value of each of the color arrays to serve as the original color information corresponding to the region of interest after excluding an outlier in each of the color arrays and executing a low-pass filtering.

In an embodiment of the invention, the image analysis method further includes: transmitting the prompt signal to a cloud server to transmit the prompt signal to a medical center via the cloud server.

The image analysis apparatus of the invention includes: an image capturing unit, a storage unit, and a processing unit. The image capturing unit captures an image under test of a dialysis bag. The storage unit includes a database. The processing unit is coupled to the image capturing unit and the storage unit and executes an analysis procedure on the image under test, wherein the analysis procedure includes: executing an edge detection on the image under test to obtain a region of interest; executing a color detection on a plurality of pixels included in the region of interest to obtain original color information corresponding to the region of interest; executing a color correction on the original color information to obtain corrected color information; converting the corrected color information to a color location in a color space; and comparing the color location with a plurality of disease warning ranges recorded in the database. The image capturing unit continues to capture another image under test of another dialysis bag for the processing unit to execute the analysis procedure on the another image under test and to send a prompt signal when detecting that the color locations of a plurality of the images under test captured in a time period gradually becomes close to one of the disease warning ranges after continuously executing the analysis procedure on a plurality of the images under test.

Based on the above, according to the invention, chrominance of the peritoneal dialysis recovered solution is detected by image analysis, which allows the user to monitor the health condition by himself/herself as a precaution against complications.

To make the aforementioned and other features and advantages of the invention more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate exemplary embodiments of the invention and, together with the description, serve to explain the principles of the invention.

DESCRIPTION OF THE EMBODIMENTS

Figure 1:
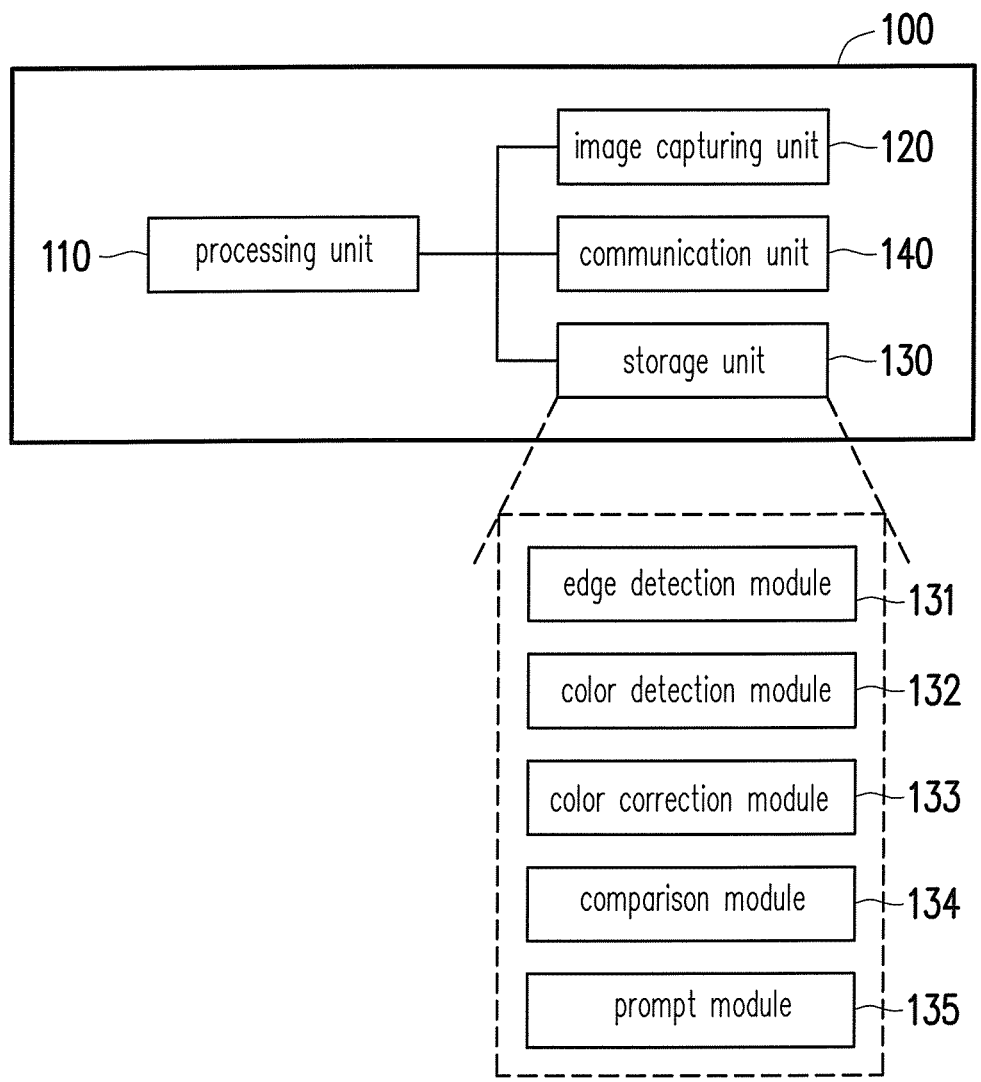
FIG. 1 is a block diagram of an image analysis apparatus according to an embodiment of the invention.

FIG. 1 is a block diagram of an image analysis apparatus according to an embodiment of the invention. With reference to FIG. 1, an image analysis apparatus 100 includes a processing unit 110, an image capturing unit 120, and a storage unit 130, and selectively includes a communication unit 140. The image analysis apparatus 100 is an electronic device, such as a smart phone and a tablet computer, which has computing capability and may communicate with a cloud server via a network service, for example.

The processing unit 110 is a central processing unit (CPU), a microprocessor, or a digital signal processor (DSP), for example. The image capturing unit 120 is a video camera or a camera that uses a CCD (charge coupled device) lens, a CMOS (complementary metal oxide semiconductor transistors) lens, or an infrared lens, for example. The storage unit 130 is a non-volatile memory (NVM), a random access memory (RAM), or a hard disk, for example. The communication unit 140 is a wired or wireless network card, for example.

This embodiment is realized by a code. For example, the storage unit 130 stores a plurality of code segments therein. The code segments are executed by the processing unit 110 after being installed to perform image analysis on a dialysis bag. For example, the storage unit 130 includes a plurality of modules, by which a plurality of functions are executed respectively. Each module includes one or more code segments. For example, the storage unit 130 includes an edge detection module 131, a color detection module 132, a color correction module 133, a comparison module 134, and a prompt module 135.

Figure 2:
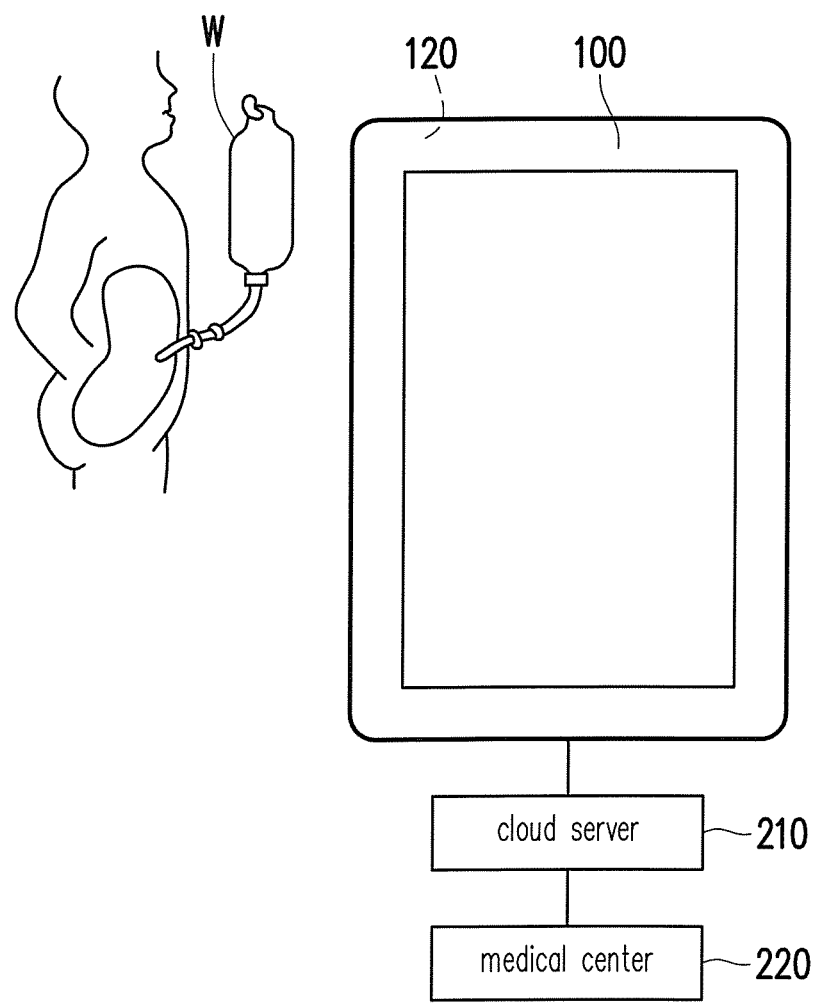
FIG. 2 is a schematic diagram of a remote care system according to an embodiment of the invention.

The image analysis apparatus 100 described above may be realized in a remote care system, an example of which is explained below. FIG. 2 is a schematic diagram of the remote care system according to an embodiment of the invention. With reference to FIG. 2, in this embodiment, the image analysis apparatus 100 is a smart phone. The user uses the image capturing unit 120 (e.g. a front camera lens or a rear camera lens) disposed on the image analysis apparatus 100 to capture an image of a dialysis bag W as an image under test. Then, the processing unit 110 executes each module in the storage unit 130 to execute an analysis procedure on the image under test, so as to obtain a color location in a color space corresponding to the image under test. The processing unit 110 continues to execute the analysis procedure on a plurality of images under test. Then, when the processing unit 110 detects that the color locations of the images under test obtained in a time period gradually become close to a disease warning range, the processing unit 110 sends a prompt signal to remind the user. The processing unit 110 may further transmit the prompt signal to a cloud server 210 via the communication unit 140 and transmit the prompt signal to a designated medical center 220 via the cloud server 210. The medical center 220 is an electronic device, such as a host or a server in a hospital, for example.

Moreover, in other embodiments, the processing unit 110 may directly upload the image under test to the cloud server 210 via the communication unit 140 for the cloud server 210 to execute the analysis procedure on the image under test. For example, the processing unit 110 transmits corrected color information and the image under test to the cloud server 210 via the communication unit 140 to be compared in the cloud server 210, and then the cloud server 210 sends back the prompt signal to the image analysis apparatus 100 of the peritoneal dialysis user.

Figure 3:
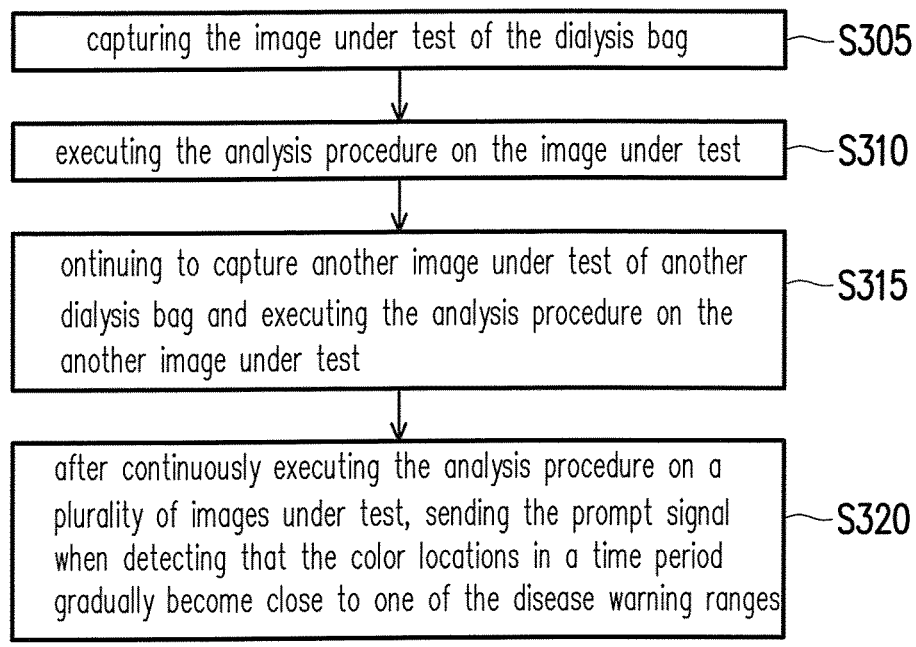
FIG. 3 is a flowchart showing an image analysis method for assessment of peritoneal dialysis complications in peritoneal dialysis according to an embodiment of the invention.

FIG. 3 is a flowchart showing an image analysis method for peritoneal dialysis according to an embodiment of the invention. With reference to FIG. 1 to FIG. 3, in Step S305, the image under test of the dialysis bag W is captured by the image capturing unit 120. For example, after the user executes the peritoneal dialysis operation and replaces the solution to obtain a peritoneal dialysis recovered solution, the lens of the image capturing unit 120 is aligned with the dialysis bag W containing the peritoneal dialysis recovered solution to capture the image under test.

Figure 4:
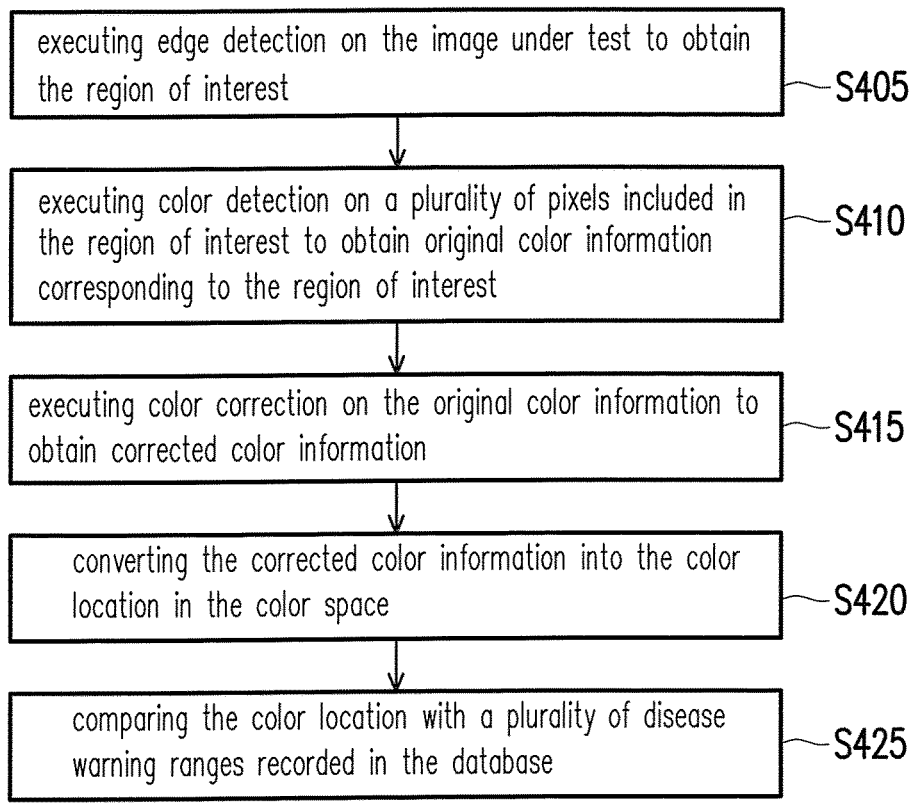
FIG. 4 is a flowchart showing an analysis procedure of an image under test according to an embodiment of the invention.

Next, in Step S310, the processing unit 110 executes the analysis procedure on the image under test. An example is described hereinafter to explain each step of the analysis procedure of the image under test. FIG. 4 is a flowchart showing the analysis procedure of the image under test according to an embodiment of the invention. With reference to FIG. 4, in Step S405, the processing unit 110 executes edge detection on the image under test by the edge detection module 131, so as to obtain a region of interest (ROI). For example, the edge detection module 131 calculates difference value between adjacent pixels in the gray scale layer of red color (R), difference value between adjacent pixels in the gay scale layer of green color (G) and difference value between adjacent pixels in the gray scale layer of blue color (B), and then combines the calculated gray scale layers together. Generally, the edge detection may be performed by using a Sobel operator or a Canny operator.

Here, in order to prevent bubbles in the liquid or reflection from causing errors in judgment, the edge detection is executed on the image under test first to highlight the locations of the bubbles and the reflective areas. After the edge detection, a target region is obtained from the image under test (i.e. the region corresponding to the dialysis bag W). The processing unit 110 may directly use this target region as the region of interest or the processing unit 110 may retrieve a preset range from the target region to serve as the region of interest, or the processing unit 110 may select a region from the target region as the region of interest according to the user's choice.

Then, in Step S410, the processing unit 110 executes color detection on a plurality of pixels included in the region of interest by the color detection module 132, so as to obtain original color information corresponding to the region of interest. For example, the processing unit 110 respectively extracts red color (R), green color (G), and blue color (B) from each pixel of the region of interest, so as to obtain three color arrays (respectively corresponding to R, G, and B). Then, after an outlier in each color array is excluded, low-pass filtering is executed on the color array, in which the outlier has been excluded, to obtain an average value of each color array after the low-pass filtering, and the average values respectively corresponding to the three colors R, G, and B are used as the original color information corresponding to the region of interest. A threshold value of the outlier may be obtained by using a 92.7% confidence interval or a box-plot.

Following that, in Step S415, the processing unit 110 executes color correction on the original color information by the color correction module 133, so as to obtain corrected color information. Generally, the image capturing unit 120 may have a built-in algorithm, which adds some non-linear components to the color information outputted by a photosensitive element for eliminating a gamma effect that may appear on a display. Accordingly, in this embodiment, the color correction module 133 has a function to restore the color information that may be non-linear to the original linear color information. In addition, in the process of color correction, the light intensity may be weighted in particular environment systems to improve exposure problems. In an embodiment, a camera module of the image capturing unit 120 first adopts matrix metering to avoid unbalanced light intake. Moreover, correct exposure may be achieved for all pixels by performing a white paper test, namely, taking a photo of a white paper under a non-uniform light source condition and normalizing all the pixels in the photo.

Here, the color correction module 133 uses a color correction matrix to execute the color correction. Take a color checker with 24 (6×4) colors as an example, linear regression calculation is executed on red color (R), green color (G), and blue color (B) of a plurality of color patches in the bottom row (ex. gray color including black, dim gray, gray, light gray, white smoke, white) of the color checker to obtain a set of regressed color parameters. Then, linear regression calculation is executed on red color (R), green color (G), and blue color (B) of all the color patches of the color checker according to the regressed color parameters to obtain the color correction matrix.

For example, the following equation (A) is a third-order linear regression calculation equation.

$$y = ax^4 + bx^3 + cx^2 + dx + e \qquad (A)$$

Pixels in a range of 30×30 are extracted from each color patches (6 in total) in the bottom row of the 6×4 color checker for executing sRGB retrieval. Then, linear regression calculation is respectively performed for R, G, and B based on the equation A, so as to obtain a parameter (a, b, c, d, e) respectively corresponding to R, G, and B, i.e. parameter (a1, b1, c1, d1, e1), parameter (a2, b2, c2, d2, e2), and parameter (a3, b3, c3, d3, e3). Thereafter, R', G', and B' are generated based on the equation (A), the three groups of parameters, and the originally extracted sRGB color values, as shown by the following equations (A1) to (A3).

$$R' = a1R^4 + b1R^3 + c1R^2 + d1R + e1 \qquad (A1)$$

$$G' = a2G^4 + b2G^3 + c2G^2 + d2G + e2 \qquad (A2)$$

$$B' = a3B^4 + b3B^3 + c3B^2 + d3B + e3 \qquad (A3)$$

Next, linear regression calculation is performed on R, G, and B of all the color patches (24 color patches in total) of the color checker according to the regressed color parameters R', G', and B', so as to obtain a color correction matrix of n×3. Here, n is an integer larger than or equal to 3.

Take an 8×3 color correction matrix for example, the linear regression calculation of R" is as shown by the following equation (B), and G" and B" may be obtained accordingly. In addition, ΔE (Euclidean distance) may be used to indicate a correction benefit.

$$R'' = a1R' + b1G' + c1B' + d1R'G' + e1R'B' + f1G'B' + g1R'G'B' + h1 \qquad (B)$$

A regression module required may be selected with reference to an augmented matrix. Please refer to Table 1 below, wherein more accurate correction is achieved as m increases.

TABLE 1

| m × 3 | augmented matrix |
|---|---|
| 3 × 3 | [R G B] |
| 5 × 3 | [R G B RGB 1] |
| 7 × 3 | [R G B RG RB GB 1] |
| 8 × 3 | [R G B RG RB GB RGB 1] |
| 10 × 3 | [R G B RG RB GB $R^2$ $G^2$ $B^2$ 1] |
| 11 × 3 | [R G B RG RB GB $R^2$ $G^2$ $B^2$ RGB 1] |
| 14 × 3 | [R G B RG RB GB $R^2$ $G^2$ $B^2$ RGB $R^3$ $G^3$ $B^3$ 1] |
| 16 × 3 | [R G B RG RB GB $R^2$ $G^2$ $B^2$ RGB $R^2$G $G^2$B $B^2$R $R^3$ $G^3$ $B^3$] |
| ... | |

Following that, in Step S420, the corrected color information is converted into the color location in the color space by the color correction module 133. Here, the color space is a CIE Lab color space. Then, in Step S425, the color location is compared with a plurality of disease warning ranges recorded in a database. In this embodiment, the storage unit 130 includes the database therein for recording a plurality of disease warning ranges. The disease warning ranges are determined through the doctor's judgment by analyzing data that is collected by gathering a large number of peritoneal dialysis recovered solutions from patients.

After the processes of the aforementioned Steps S405 to S420, the color location of the peritoneal dialysis recovered solution is obtained, and a relationship between the color location and each disease warning range is calculated by using the Euclidean distance.

Reverting to FIG. 3, in Step S315, the image capturing unit 120 continues to capture the images under test of other dialysis bags and execute the analysis procedure on the images under test. Because the user needs to constantly perform the peritoneal dialysis and replace the solution several times every day, the dialysis bag of the peritoneal dialysis recovered solution may be photoed whenever the peritoneal dialysis operation is performed and the peritoneal dialysis recovered solution is retrieved by solution replacement, so as to execute the analysis procedure on the obtained image under test (as shown in Steps S405 to S425).

Then, in Step S320, after the analysis procedure is continuously executed on a plurality of images under test, the processing unit 110 sends the prompt signal by the prompt module 135 when detecting that the color locations of the images under test obtained in a time period gradually become close to one of the disease warning ranges. In other words, the Euclidean distance between the color location that is obtained each time and the disease warning ranges in the database is calculated and recorded. The prompt signal may be sent immediately not only when the color location falls within the disease warning range of one disease, but also when the color locations obtained in a time period gradually become close to the disease warning range (not within the disease warning range yet) according to the distance relationship that is recorded each time. The time period may be 1 day, 2 days, or 3 days, for example. Accordingly, by transmitting the prompt signal to the medical center 220 via the cloud server 210, the hospital may notice possible problems in advance and monitor the health condition of user remotely.

In addition, the processing unit 110 may further upload the image under test, the corrected color information, and a comparison result obtained by comparing the color location and the disease warning range recorded in the database to the cloud server 210 via the communication unit 140. Regarding the timing of the upload, the image under test, the corrected color information, and the comparison result may be uploaded immediately respectively after the same is obtained. Alternatively, the image under test, the corrected color information, and the comparison result may be uploaded at an uploading time that is preset.

In conclusion, according to the invention, chrominance of the peritoneal dialysis recovered solution is detected by image analysis, which is applicable to electronic devices, such as a smart phone and a tablet computer, and allows the user to monitor the health condition by himself/herself as a precaution against complications. Moreover, communication with the hospital may be achieved timely via the network services and the cloud server for remote monitoring.

It will be apparent to those skilled in the art that various modifications and variations can be made to the disclosed embodiments without departing from the scope or spirit of the invention. In view of the foregoing, it is intended that the invention covers modifications and variations provided that they fall within the scope of the following claims and their equivalents.

What is claimed is:

1. An image analysis method for assessment of a peritoneal dialysis complication in peritoneal dialysis, comprising:
   capturing an image under test of a dialysis bag;
   executing an analysis procedure on the image under test, comprising:
      executing an edge detection on the image under test to obtain a region of interest;
      executing a color detection on a plurality of pixels included in the region of interest to obtain original color information corresponding to the region of interest;
      executing a color correction on the original color information to obtain corrected color information;
      converting the corrected color information to a color location in a color space; and
      comparing the color location with a plurality of disease warning ranges recorded in a database;
   continuing to capture another image under test of another dialysis bag and executing the analysis procedure on the another image under test; and
   after continuously executing the analysis procedure on a plurality of the images under test, sending a prompt signal when detecting that the color locations of the images under test captured in a time period gradually becomes close to one of the disease warning ranges.

2. The image analysis method according to claim 1, further comprising:
   executing a linear regression calculation on red color, green color, and blue color of a plurality of color patches in a bottom row of a color checker to obtain a set of regressed color parameters; and
   executing the linear regression calculation on red color, green color, and blue color of all color patches of the color checker according to the set of regressed color parameters to obtain a color correction matrix,
   wherein the step of executing the color correction on the original color information to obtain the corrected color information comprises:
      executing the color correction on the original color information based on the color correction matrix to obtain the corrected color information.

3. The image analysis method according to claim 1, further comprising:
   uploading the image under test, the corrected color information, and a comparison result obtained by comparing the color location with the disease warning ranges recorded in the database to a cloud server.

4. The image analysis method according to claim 1, wherein the color space is a CIE Lab color space.

5. The image analysis method according to claim 1, wherein the step of executing the color detection on the pixels included in the region of interest to obtain the original color information corresponding to the region of interest comprises:
   respectively extracting red color, green color, and blue color from each of the pixels of the region of interest to obtain three color arrays; and
   retrieving an average value of each of the color arrays to serve as the original color information corresponding to the region of interest after excluding an outlier in each of the color arrays and executing a low-pass filtering.

6. The image analysis method according to claim 1, further comprising:
   transmitting the prompt signal to a cloud server to transmit the prompt signal to a medical center via the cloud server.

7. An image analysis apparatus, comprising:
   an image capturing unit capturing an image under test of a dialysis bag;
   a storage unit comprising a database; and
   a processing unit coupled to the image capturing unit and the storage unit and executing an analysis procedure on the image under test, wherein the analysis procedure comprises: executing an edge detection on the image under test to obtain a region of interest; executing a color detection on a plurality of pixels included in the region of interest to obtain original color information corresponding to the region of interest; executing a color correction on the original color information to obtain corrected color information; converting the corrected color information to a color location in a color space; and comparing the color location with a plurality of disease warning ranges recorded in the database,
   wherein the image capturing unit continues to capture another image under test of another dialysis bag for the processing unit to execute the analysis procedure on the another image under test and to send a prompt signal when detecting that the color locations of a plurality of the images under test captured in a time period gradually becomes close to one of the disease warning ranges after continuously executing the analysis procedure on a plurality of the images under test.

8. The image analysis apparatus according to claim 7, wherein the processing unit executes a linear regression calculation on red color, green color, and blue color of a plurality of color patches in a bottom row of a color checker to obtain a set of regressed color parameters; and executes the linear regression calculation on red color, green color, and blue color of all color patches of the color checker according to the set of regressed color parameters to obtain a color correction array; and the processing unit executes the color correction on the original color information based on the color correction array in the analysis procedure to obtain the corrected color information.

9. The image analysis apparatus according to claim 7, further comprising:

a communication unit coupled to the processing unit, wherein the processing unit is connected to a network via the communication unit to upload the image under test, the corrected color information, and a comparison result obtained by comparing the color location with the disease warning ranges recorded in the database to a cloud server; and the processing unit transmits the prompt signal to the cloud server via the communication unit to transmit the prompt signal to a medical center via the cloud server.

10. The image analysis apparatus according to claim 7, wherein the processing unit respectively extracts red color, green color, and blue color from each of the pixels of the region of interest to obtain three color arrays; and retrieves an average value of each of the color arrays to serve as the original color information corresponding to the region of interest after excluding a outlier in each of the color arrays and executing a low-pass filtering.

* * * * *